US007939513B2

(12) United States Patent
Takhi et al.

(10) Patent No.: US 7,939,513 B2
(45) Date of Patent: May 10, 2011

(54) TETRACYCLINE DERIVATIVES AS ANTIBACTERIAL AGENTS

(75) Inventors: Mohamed Takhi, Hyderabad (IN); Natesan Selvakumar, Bangalore (IN); Sreenivas Kandepu, Hyderabad (IN); Gavara Govinda Rajulu, Hyderabad (IN); Javed Iqbal, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 12/231,973

(22) Filed: Sep. 8, 2008

(65) Prior Publication Data

US 2009/0111776 A1 Apr. 30, 2009

Related U.S. Application Data

(60) Provisional application No. 61/053,414, filed on May 15, 2008.

(30) Foreign Application Priority Data

Sep. 7, 2007 (IN) .......................... 2008/CHE/2007

(51) Int. Cl.
*A61K 31/65* (2006.01)
*C07D 207/16* (2006.01)
(52) U.S. Cl. ..................... 514/152; 548/528; 548/579
(58) Field of Classification Search .................. 514/152; 548/528, 579
See application file for complete search history.

(56) References Cited

U.S. PATENT DOCUMENTS

| | | | | |
|---|---|---|---|---|
| 5,328,902 A | | 7/1994 | Sum et al. | |
| 5,380,888 A | * | 1/1995 | Sum et al. | 552/205 |
| 5,401,729 A | * | 3/1995 | Sum et al. | 514/152 |
| 5,466,684 A | * | 11/1995 | Sum et al. | 514/152 |
| 5,494,903 A | | 2/1996 | Hlavka et al. | |
| 5,495,031 A | * | 2/1996 | Sum et al. | 552/206 |
| 7,323,492 B2 | | 1/2008 | Huss et al. | |
| 7,326,696 B2 | | 2/2008 | Nelson et al. | |
| 2004/0242548 A1 | | 12/2004 | Draper et al. | |
| 2006/0183720 A1 | | 8/2006 | Sum et al. | |

FOREIGN PATENT DOCUMENTS

EP 0 582 788 A1 2/1994

OTHER PUBLICATIONS

PCT International Search Report, mailed Dec. 30, 2008, completed Dec. 18, 2008, PCT Patent Application No. PCT/US2008/010462, filed Sep. 8, 2008, Dr. Reddy's Laboratories Ltd.
1945 and entered widespread clinical use in 1948 (Duuam BM, *Aureomycin: product of continuing search for new antibiotics*. Ann. NY Acas Sci 1948 51, 177-181).
Chopra I et.al., *Tetracylines, molecular and clinical aspects. J. Antimicro. Chemother* 1992, 29, 245-277.
R. B. Silverman, 1992, "The Organic Chemistry of Drug Design and Drug Action", Academic Press, Chp. 8.
Berge et al. (1977) "Pharmaceutical Salts", J. Pharm. Sci. 66:1-19.
Fifth edition of Approved Standards NCCLS document *M7-A5* vol. 20-No. 2, 2000 Villinova, PA (Currently *Clinical and Laboratory Standards Institute (CLSI)*.
Jan G. Den Hollander, Jenny D. Knudsen, Johan W. Mouton, Kurt Fuursted, Niels Frimodt-Moller, Henri A. Verbrugh and Frank Espersen. Comparison of Pharmacodynamics of Azithromycin and Erythromycin In Vitro and In Vivo. Antibacterial agents and chemotherapy. Feb. 1998, p. 377-382 vol. 42, No. 2.
Hiroki Okamoto, Shuichi Miyazaki, Kazuhiro Tateda, Yoshikazu Ishii and Keizo Yamaguchi. In Vivo Efficacy of Telithromycin (HMR3647) against *Streptococcus pneumoniae* and *Haemophilus influenzae*. Antibacterial agents and chemotherapy Nov. 2001, p. 3250-3252 vol. 45, No. 11.
PCT Notification Concerning Tramsmittal of International Preliminary Report on Patentability Search and PCT International Preliminary Report on Patentability, The International Bureau of WIPO, mailed Mar. 18, 2010, date of issuance of report, Mar. 9, 2010, International Application No. PCT/US2008/010485, International Filing Date Sep. 8, 2008, Dr. Reddy's Laboratories Ltd. et al.
PCT Notification Concerning Transmittal of International Preliminary Report on Patentability Search and PCT International Preliminary Report on Patentability, The International Bureau of WIPO, mailed Mar. 18, 2010, date of issuance of report, Mar. 9, 2010, International Application No. PCT/US2008/010462, International Filing Date Sep. 8, 2008, Dr. Reddy's Laboratories Ltd. et al.
PCT International Search Report and Written Opinion of the Internatonal Searching Authority, actual completion date Apr. 17, 2009, date of mailing Apr. 24, 2009, European Patent Office, International Application No. PCT/US2008/010485, International Filing Date Sep. 8, 2008, Applicant Dr. Reddy's Laboratories Ltd.

* cited by examiner

*Primary Examiner* — Sabiha Qazi
(74) *Attorney, Agent, or Firm* — Balaram Gupta; Robert A. Franks; Thomas C. McKenzie

(57) ABSTRACT

In accordance with one aspect, the present invention provides a compound of general formula (I), its stereoisomers thereof and/or its pharmaceutically acceptable salts thereof, which have antibacterial activity; with methods of treating infectious diseases in warm blooded animals employing these new compounds.

(I)

wherein
$R_1$ is selected from optionally substituted alkyl.

16 Claims, No Drawings

TETRACYCLINE DERIVATIVES AS ANTIBACTERIAL AGENTS

RELATED APPLICATIONS

This application claims priority to Indian Patent Application No. 2008/CHE/2007 filed Sep. 7, 2007 and U.S. Provisional Patent Application No. 61/053,414 filed on May 15, 2008.

FIELD OF THE INVENTION

The present invention relates to novel tetracycline derivatives of formula (I), stereoisomers thereof and/or pharmaceutically acceptable salts thereof, which exhibit antibiotic activity against a wide spectrum of microorganisms and are useful as antibiotic agents.

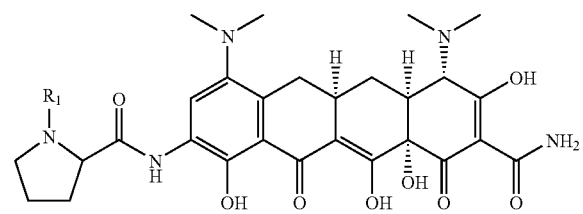

BACKGROUND OF THE INVENTION

The tetracyclines as a class of antibiotics were first identified in 1945 and entered widespread clinical use in 1948 (Duuam B M, *Aureomycin: product of continuing search for new antibiotics*. Ann. NY Acas Sci 1948 51, 177-181). Two years later, oxytetracycline became available. The elucidation of the chemical structure of these compounds confirmed their similarity and furnished the analytical basis for the production of a third member of this group in 1952, tetracycline. A new family of tetracycline derivatives, without the ring-attached methyl group present in earlier tetracyclines, was prepared in 1957 and became publicly available in 1967; and minocycline was in use by 1972. Historically, soon after their initial development and introduction, the tetracyclines were found to be highly effective pharmacologically against rickettsiae; a number of Gram-positive and Gram-negative bacteria; and the agents responsible for lymphogranuloma venereum, inclusion conjunctivitis, and psittacosis. Tetracyclines are active not only against Gram-positive and Gram-negative bacteria, but also against those bacteria lacking cell walls, bacteria that live within cells and anerobic bacteria Refer Chopra I et. al., *Tetracylines, molecular and clinical aspects. J. Antimicro. Chemother* 1992, 29, 245-277. Hence, tetracyclines became known as "broad spectrum" antibiotics.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline derivatives.

SUMMARY OF THE INVENTION

In accordance with one aspect, the present invention provides a compound of general formula (I), its stereoisomers thereof and/or its pharmaceutically acceptable salts thereof, which have antibacterial activity; with methods of treating infectious diseases in warm blooded animals employing these new compounds.

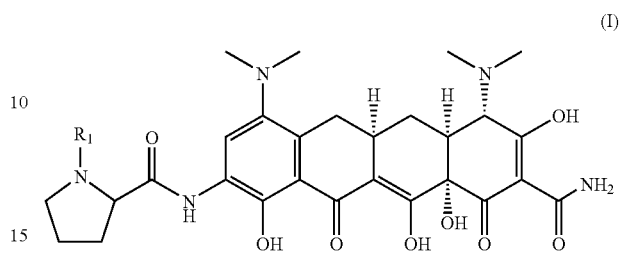

wherein $R_1$ is selected from optionally substituted alkyl.

In yet another aspect, the present invention, provides stereoisomers of general formula (I), having the general formula (II)

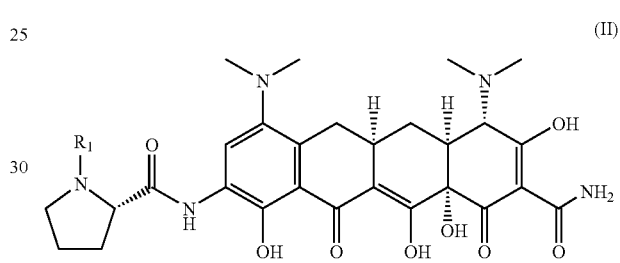

its pharmaceutical acceptable salts thereof;

wherein $R_1$ is selected from optionally substituted alkyl.

In yet another aspect, the present invention, provides stereoisomers of general formula (I), having the general formula (III)

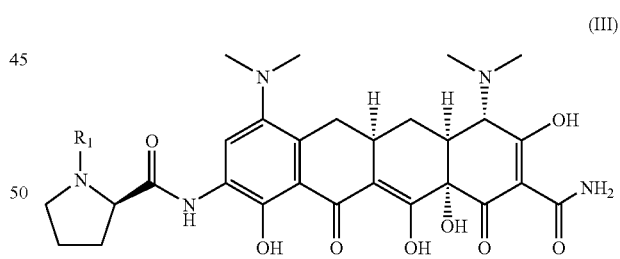

its pharmaceutical acceptable salts thereof;

wherein $R_1$ is selected from optionally substituted alkyl.

More particularly, this invention is related to the specific compounds of formula (I), including its stereoisomers and/or pharmaceutically acceptable salts, which have enhanced antibacterial activity against tetracycline resistant strains as well as activity against strains which are normally susceptible to tetracyclines.

In accordance with other aspect, the present invention provides a pharmaceutical composition comprising a compound having the general formula (I), its stereoisomer thereof and/or its pharmaceutically acceptable salts thereof and one or more pharmaceutically acceptable excipients.

In accordance with other aspect, the present invention provides a method of treating or preventing a bacterial disease in an individual comprising administering to said individual a therapeutically effective amount of a compound having the general formula (I), its stereoisomer thereof and/or its pharmaceutically acceptable salts thereof, and one or more pharmaceutically acceptable excipients.

DETAILED DESCRIPTION OF THE INVENTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

ABBREVIATIONS AND DEFINITIONS

As used herein, the term "alkyl," is intended to include both branched and straight-chain saturated aliphatic hydrocarbon groups having a specified number of carbon atoms. Exemplary alkyl groups of the invention have from 1 to 10 carbon atoms. Branched means a lower alkyl group such as methyl, ethyl or propyl, is attached to a linear alkyl chain. Non-limiting examples of suitable alkyl groups include methyl, ethyl, n-propyl, isopropyl, n-butyl, and t-butyl.

As used herein, the term 'optionally substituted' means that substitution is optional and therefore it is possible for the designated atom or molecule to be unsubstituted. In the event a substitution is desired, then such substitution means that any number of hydrogens on the designated atom is replaced with a selection from the indicated group, provided that the normal valency of the designated atom is not exceeded, and that the substitution results in a stable compound. If no selection is provided in formula I then the substituent may be selected from one or more of —$OC_{1-6}$ alkyl, —$C_{1-6}$alkyl, F, Cl, Br, —$NH_2$, and —OH.

As used herein, the terms "treatment," "treating," "treat," and the like are used to refer generally to obtaining a desired pharmacological and/or physiological effect. The effect may be prophylactic in terms of completely or partially p1)reventing a disease or symptom thereof and/or may be therapeutic in terms of a partial or complete stabilization or cure for a disease and/or adverse effect attributable to the disease. "Treatment" as used herein covers any treatment of a disease in a subject, particularly a human, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

As used herein, the terms "therapeutically effective amount" refer to the amount of a compound of formula (I) that will elicit the biological or medical response of a tissue, system, or patient that is being sought.

As used herein, the term "pharmaceutically acceptable carrier" includes substances capable of being coadministered with the tetracycline derivatives of general formula (I) and which allow the tetracycline derivatives of general formula (I) to perform their intended function(s), e.g., to treat or prevent bacterial infections. Suitable pharmaceutically acceptable carriers include but are not limited to one or more of water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like.

Compounds of formula (I) contain more than one asymmetric carbons. It is to be understood accordingly that the stereoisomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. For any particular compound disclosed herein, any general structure presented also encompasses all conformational isomers, regioisomers, stereoisomers and tautomers that may arise from a particular set of substituents. The general structure also encompasses all enantiomers, diastereomers, and other optical isomers whether in enantiomeric or racemic forms, as well as mixtures of stereo isomers, as the context requires. The general structure also encompasses all pharmaceutically acceptable salts and prodrugs thereof.

In accordance with one aspect, the present invention provides a compound of general formula (I), its stereoisomers thereof, and/or its pharmaceutically acceptable salts thereof, which have antibacterial activity; with methods of treating infectious diseases in warm blooded animals employing these new compounds.

(I)

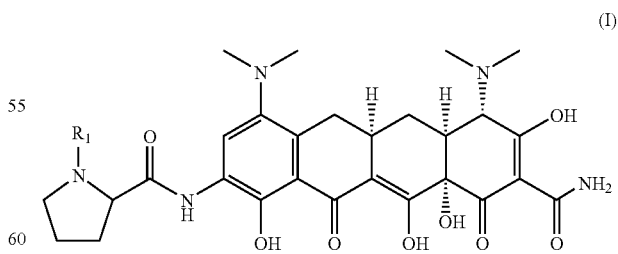

wherein $R_1$ is selected from optionally substituted alkyl.

In yet another aspect, the present invention, provides stereoisomers of general formula (I), having the general formula (II)

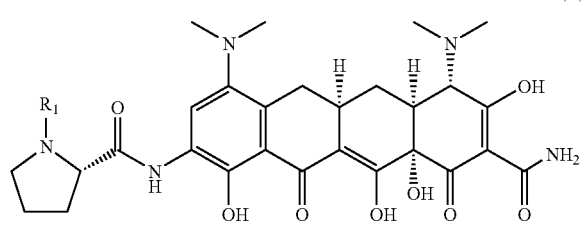

(II)

and/or its pharmaceutical acceptable salts thereof;
wherein
R₁ is selected from optionally substituted alkyl.

In yet another aspect, the present invention, provides stereoisomers of general formula (I), having the general formula (III)

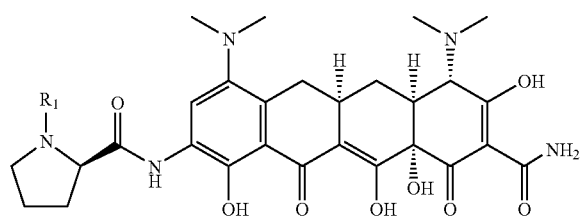

(III)

and/or its pharmaceutical acceptable salts thereof;
wherein
R₁ is selected from optionally substituted alkyl.

Another embodiment of the present invention provides compounds of formula (I),
wherein R₁ is (C₁-C₅) alkyl.

Another embodiment of the present invention provides compounds of formula (I),
wherein R₁ is methyl, ethyl, n-propyl, iso-propyl, n-butyl or iso-butyl.

Another embodiment of the present invention provides a compound of general formula (I), which comprises:

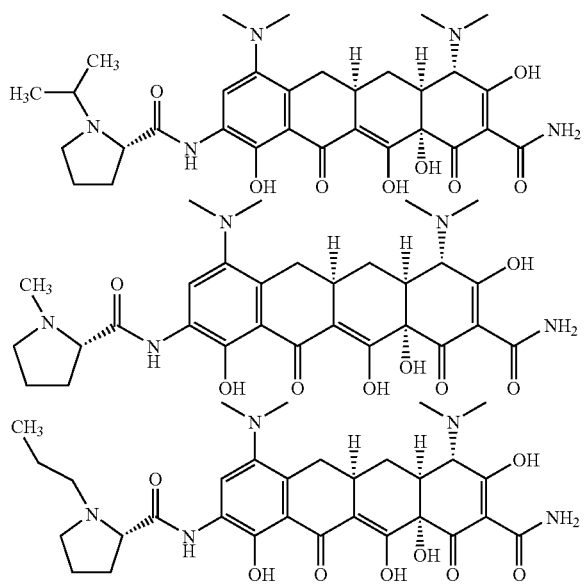

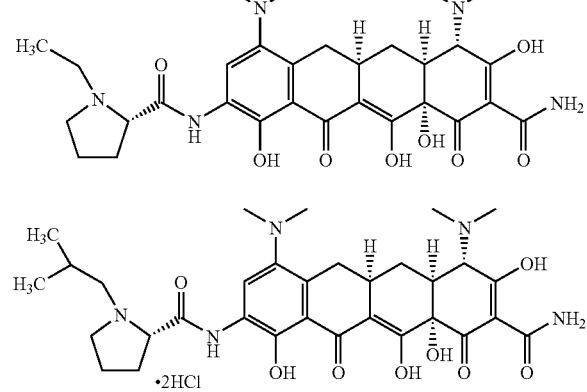

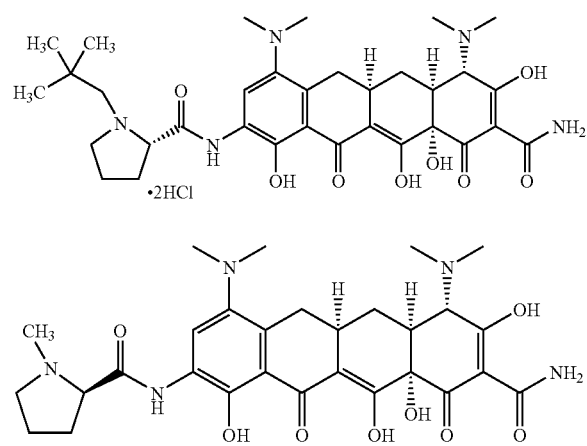

and/or pharmaceutically acceptable salts thereof.

Another embodiment of the present invention provides the tetracycline derivative of formula (I), which has the structure

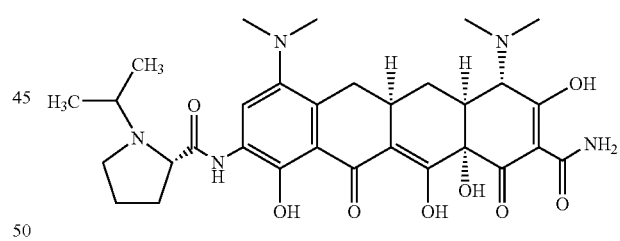

and/or its pharmaceutical acceptable salts thereof;

Another embodiment of the present invention provides the tetracycline derivative of formula (I), which has the structure

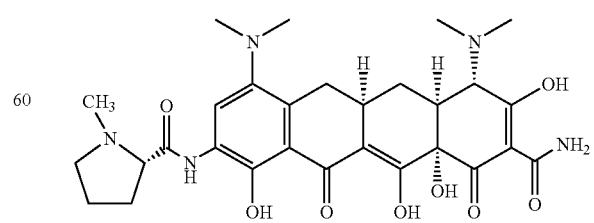

and/or its pharmaceutical acceptable salts thereof;

Another embodiment of the present invention provides the tetracycline derivative of formula (I), which has the structure

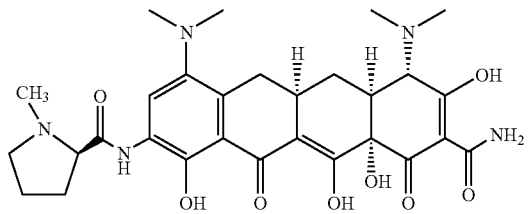

and/or its pharmaceutically acceptable salts thereof;

Another embodiment of the present invention provides the tetracycline derivative of formula (I), which has the structure

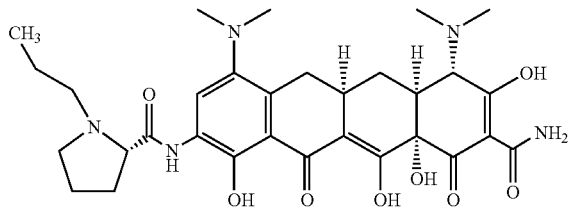

and/or pharmaceutically acceptable salts thereof;

Another embodiment of the present invention provides the tetracycline derivative of formula (I), which has the structure

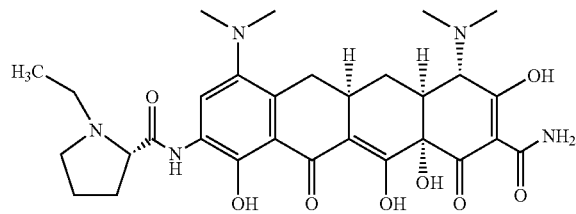

and/or pharmaceutically acceptable salts thereof;

Another embodiment of the present invention provides the tetracycline derivative of formula (I), which has the structure

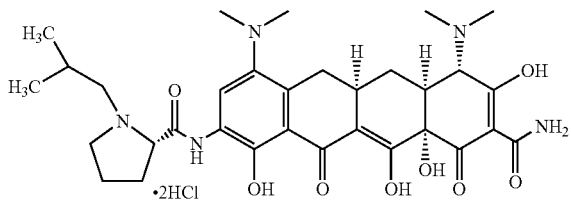

and/or pharmaceutically acceptable salts thereof;

Another embodiment of the present invention provides the tetracycline derivative of formula (I), which has the structure

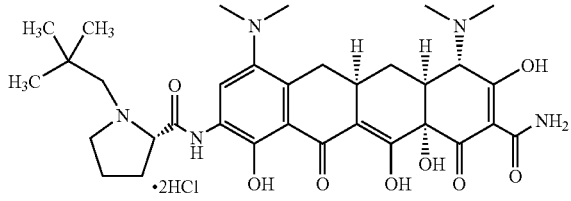

and/or pharmaceutically acceptable salts thereof;

More particularly, this invention is related to the specific compounds of formula (I), which have enhanced antibacterial activity against tetracycline resistant strains as well as activity against strains which are normally susceptible to tetracyclines.

In accordance with another aspect, the present invention provides a pharmaceutical composition comprising a compound having the general formula (I), stereoisomers thereof and/or pharmaceutically acceptable salt thereof and one or more pharmaceutically acceptable excipients.

In accordance with another aspect, the present invention provides a method of treating or preventing a bacterial disease in an subject comprising administering to the subject a therapeutically effective amount of a compound having the general formula (I), stereoisomers thereof and/or pharmaceutically acceptable salts thereof, and one or more pharmaceutically acceptable excipients.

According to another embodiment of the present invention, novel tetracycline derivatives of formula (I) are provided that are useful for the treatment or prevention of bacterial disease.

As will be recognized by those having ordinary skill in the art, the compounds of the present invention may be basic in nature, and may be capable of forming a wide variety of salts with various inorganic and organic acids. The acids that may be used to prepare pharmaceutically acceptable acid addition salts of the tetracycline compound of the present invention include those that form non-toxic acid addition salts, i.e., salts containing pharmaceutically acceptable anions, including, but not limited to, hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)]salts.

Although such salts are typically pharmaceutically acceptable for administration to a subject, e.g., a mammal, it may be desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt.

The acid addition salts of the base compounds of this invention may be prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline derivatives of the invention not specifically described in the experimental section may be accomplished using combinations of the reactions described above that will be apparent to those skilled in the art.

As will be recognized by those having ordinary skill in the art, compounds of the present invention that are acidic in nature may be capable of forming a wide variety of base salts. The chemical bases that are contemplated as useful as reagents to prepare pharmaceutically acceptable base salts of the present tetracycline derivatives that are acidic in nature are those pharmaceutically acceptable base salts that form non-toxic base salts with such compounds. Such non-toxic base salts may include, but are not limited to one or more of those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The pharmaceutically acceptable base addition salts of tetracycline derivatives of the present invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, may be under reduced pressure. Alternatively, a lower alkyl alcohol solution of the tetracycline compound of the invention may be mixed with an alkoxide of the desired metal and the solution subsequently evaporated to dryness. The present invention also pertains to methods of treating bacterial infections and associated diseases. The methods include administration of an effective amount of one or more tetracycline compound of general formula (I) to a subject. The subject can be a mammal, such as pets (e.g., cats, dogs, ferrets, etc.), farm animals (cows, sheep, pigs, horses, goats, etc.), lab animals (rats, mice, monkeys, etc.), and primates (chimpanzees, humans, gorillas).

Prodrugs are compounds which are converted in vivo to active forms (see, e.g., R. B. Silverman, 1992, "The Organic Chemistry of Drug Design and Drug Action", Academic Press, Chp. 8). Prodrugs may be used to alter the biodistribution (e.g., to allow compounds which would not typically enter the reactive site of the protease) or the pharmacokinetics for a particular compound. For example, a hydroxyl group may be esterified, e.g., with a carboxylic acid group to yield an ester. When the ester is administered to a subject, the ester is cleaved, enzymatically or non-enzymatically, reductively or hydrolytically, to reveal the hydroxyl group. Also $CONH_2$ may link with appropriate groups and form prodrugs, which may cleave in in vivo.

The term "prodrug moiety" includes moieties which can be metabolized in vivo to a hydroxyl group and moieties which may advantageously remain esterified in vivo. In some embodiments, prodrug moieties of the present invention may be metabolized in vivo by esterases or by other mechanisms to hydroxyl groups or other advantageous groups. Examples of prodrugs and their uses are well known in the art (See, e.g., Berge et al. (1977) "Pharmaceutical Salts", J. Pharm. Sci. 66:1-19).

Desirable prodrugs may be prepared in situ during the final isolation and purification of the present compounds, or by separately reacting the purified compound in its free acid form or hydroxyl with a suitable esterifying agent. Hydroxyl groups may be converted into esters via treatment with a carboxylic acid. Examples of prodrug moieties include, but are not limited to, one or more of substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Exemplary prodrug moieties may be propionoic acid esters and acyl esters.

Bacterial infections may be caused by a wide variety of gram positive and gram negative bacteria. The compounds of the present invention are contemplated as useful as antibiotics against organisms which are resistant to other tetracyclines and resistance mediated by other classes of antibiotics (beta-lactams, macrolides, floroquinolones and glycopeptides etc.) compounds.

The tetracycline derivatives of general formula (I) may also be used to treat infections traditionally treated with tetracycline derivatives such as one or more of, for example, rickettsiae; a number of Gram-positive and Gram-negative bacteria; and the agents responsible for lymphogranuloma venereum, inclusion conjunctivitis, psittacosis. The tetracycline derivatives may be used to treat bacterial infections of sensitive and resistant strains include *K. pneumoniae, Salmonella, A. baumanii, B. catarrhalis, H. influenzae, P. aeruginosa, E. faecium, E. faecalis E. coli, S. aureus, S. Pneumonae*, and *Streptococcus* Spp. The antibiotic activity of the tetracycline derivatives of the invention may be determined using the method discussed in the following Examples 8 & 9.

The pharmaceutical preparations may be sterilised and, if desired, mixed with auxiliary agents, including, but not limited to, one or more of, lubricants, preservatives, stabilisers, wetting agents, emulsifiers, salts for influencing osmotic pressure, buffers, colourings, flavourings and/or aromatic substances and the like which do not deleteriously react with the compounds of the invention.

The compounds of the present invention may be administered in a wide variety of different dosage forms. For example, they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like, and combinations thereof. Such carriers may include one or more of solid diluents or fillers, sterile aqueous media, and various non-toxic organic solvents, etc. Moreover, oral pharmaceutical compositions may be sweetened and/or flavored. In general, the compounds of the invention may be present in such dosage forms at concentration levels ranging from about 0.1% to about 90% by weight.

For oral administration, tablets may contain various excipients such as one or more of microcrystalline cellulose, sodium citrate, calcium carbonate, dicalcium phosphate and glycine may be employed along with various disintegrants such as starch (such as corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulphate and talc may be employed. Solid compositions of a similar type may also be employed as fillers in gelatin capsules; exemplary materials in this connection may also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents, together with diluents such as water, ethanol, propylene glycol, glycerin and various combinations thereof.

For parenteral administration (including intraperitoneal subcutaneous, intravenous, intradermal or intramuscular injection), solutions of compounds of the present invention in, for example, either sesame or peanut oil or in aqueous propylene glycol may be employed. The aqueous solutions may be buffered if necessary and the liquid diluent first rendered isotonic. These aqueous solutions may be suitable for intravenous injection purposes. The oily solutions may be suitable for intraarticular, intramuscular, and/or subcutaneous injection purposes. The preparation of all these solutions under sterile conditions may be accomplished by standard pharmaceutical techniques known to those having ordinary skill in the art. For parenteral administration, examples of suitable preparations may include solutions, such as oily or aqueous or non-aqueous solutions, as well as suspensions, emulsions, and/or implants, including suppositories. Compounds of the present invention may be formulated in sterile form in multiple or single dose formats. For example, the compounds of the present invention may be dispersed in a fluid carrier such as sterile saline and/or 5% saline dextrose solutions commonly used with injectables.

In another embodiment, the compounds of the present invention may be administered topically. For example, it may be desirable to administer the compounds of the present invention topically when treating inflammatory conditions of the skin. Non-limiting examples of methods of topical administration include transdermal, buccal, or sublingual application. For topical applications, therapeutic compounds may be suitably admixed in a pharmacologically inert topical carrier such as a gel, an ointment, a lotion, and/or a cream. Such topical carriers may include water, glycerol, alcohol, propylene glycol, fatty alcohols, triglycerides, fatty acid esters, and/or mineral oils. Other possible topical carriers may include liquid petrolatum, isopropylpalmitate, polyethylene glycol, ethanol 95%, polyoxyethylene monolauriate 5% in water, sodium lauryl sulphate 5% in water, and the like, and combinations thereof. In addition, materials such as surfactants, anti-oxidants, humectants, viscosity stabilizers, and the like, and combinations thereof, also may be added if desired.

It will be appreciated by those having ordinary skill in the art that the exemplary amounts of active compounds used in a given therapy will vary according to the specific compound being utilized, the particular compositions formulated, the mode of application, the particular site of administration, etc. Optimal administration rates for a given protocol of administration may be ascertained by those having ordinary skill in the art using conventional dosage determination tests conducted with regard to the foregoing guidelines.

In general, compounds of the present invention for treatment may be administered to a subject in dosages, which are susceptible for the treatment of wide spectrum of bacterial infections. For example, a suitable effective dose of one or more compounds of the present invention may be in the range of from about 0.01 to about 100 milligrams per kilogram of body weight of recipient per day, or in the range of from about 0.5 to about 50 milligrams per kilogram body weight of recipient per day, or in the range of from about 0.1 to about 20 milligrams per kilogram body weight of recipient per day. The exemplary dose may be suitably administered once daily, or several sub-doses, e.g. 2 to 5 sub-doses, may be administered at appropriate intervals through the day, or other appropriate schedule.

The tetracycline derivatives of the formula (I), stereoisomers thereof, and/or pharmaceutically acceptable salts thereof may be administered via one or more of the oral, parenteral, or topical routes. Additionally, the tetracycline derivatives of the present invention may be administered by other routes known in the art. In general, these compounds may be administered in effective dosages, depending upon the weight and condition of the subject being treated and the particular route of administration chosen. Variations may occur depending upon the species of the subject being treated and the individual response to said medicament, as well as on the type of pharmaceutical formulation chosen and the time period and interval at which such administration is carried out.

Solvates of the compounds of general formula (I), stereoiosmers thereof and/or pharmaceutically acceptable salts thereof may be prepared by conventional methods such as dissolving the thiazole derivative in solvents such as water, methanol, ethanol and the like.

Hydrates of the compounds of general formula (I), stereoiosmers thereof and/or pharmaceutically acceptable salts thereof of the present invention require the presence of water at some stage; water may be added as a co-solvent in the process. However, it is also possible to provide sufficient water for hydrate formation by carrying out the reaction with exposure to atmospheric moisture, or by use of non-anhydrous solvents.

Various polymorphs of a compound of formula (I), stereoisomers thereof and/or pharmaceutically acceptable salts thereof may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Heating or melting the compound followed by gradual or fast cooling may also obtain polymorphs. The presence of polymorphs may be determined by IR spectroscopy, differential scanning calorimetry, powder X-ray powder diffraction pattern or such other techniques.

The tetracycline derivatives of general formula (I) demonstrate enhanced pharmacodynamic properties, as compared to prior art tetracycline derivatives, including, but not limited to, improved in vitro potency against target pathogens and improved oral bioavailability and efficacy by the oral route in in vivo infection models. These properties, which may be useful in treating patients by both oral and intravenous routes, may result in a reduction of treatment costs and times at lower doses. Moreover, a reduction of treatment times may lead to improved recovery times and/or a reduction in hospital stays.

The tetracycline compounds of general formula (I) thus prepared may be isolated and purified from the reaction mixture by known means, including but not limited to, solvent extraction, concentration, neutralization, filtration, crystallization, recrystallization, column chromatography, high performance liquid chromatography and recrystallization, to give a highly purified product of interest.

The compounds of the present invention, stereoisomers thereof, and salts thereof may be prepared by applying various synthetic methods utilizing the characteristics due to the fundamental skeleton or type of the substituents thereof. Representative production methods will be illustrated hereunder.

The following acronyms, abbreviations, terms and definitions have been used throughout the reaction scheme and experimental section:

THF (tetrahydrofuran), HCl (hydrochloride), $K_2CO_3$ (potassium carbonate), $Na_2SO_4$ (sodium sulphate), $Na_2CO_3$ (sodium carbonate), $CDCl_3$ (chloroform-d), CBz-Cl (benzyl chloroformate), $InCl_3$ (indium chloride), NaOH (sodium hydroxide), DMF (dimethylformamide), Pd/C (Palladium on Carbon), DMPU (N,N'-dimethylpropyleneurea), HPLC (high performance liquid chromatography), TLC (thin layer chromatography), min (minutes), mol (mole), mmol (milli mole), mL (milliliters), mp (melting point), rt (room temperature), aq (aqueous), min (minute), h (hr, hour), g (grams), atm (atmosphere), conc. (concentrated), MS (mass spectroscopy/spectrometry), MALDI (matrix-assisted laser desorption/ionization), NMR (nuclear magnetic resonance).

NMR Abbreviations:

br (broad), apt (apparent), s (singlet), d (doublet), t (triplet), q (quartet), dq (doublet of quartets), dd (doublet of doublets), dt (doublet of triplets), m (multiplet).

The following synthetic processes describe various embodiments of the present invention. Other embodiments within the scope of the claims herein will be apparent to one skilled in the art from consideration of the specification or practice of the invention as disclosed herein.

Synthetic Process: 1

A compound of formula (Ic) may be prepared by chlorination of a compound of formula (Ib) with reagents, such as oxalyl chloride, thionyl chloride, $PCl_5$, and the like in a solvent, such as DCM, DCC, THF and the like, for a period of from about 1 min to about 6 hours, at a temperature in the range of from about $-10°$ C. to about $100°$ C.

A compound of general formula (III) may be prepared by reacting a compound of formula (Ic) with a compound of formula (Id) in a base, such as $Na_2CO_3$, $Et_3N$, $K_2CO_3$, $NaHCO_3$, DBU, Hunig's base and the like; and at least one solvent, such as DMF, $CH_3CN$, DMSO, THF, DMPU, and the like; at a temperature in the range of from about $-10°$ C. to about $60°$ C., over a period of from about 5 min to about 2 hours.

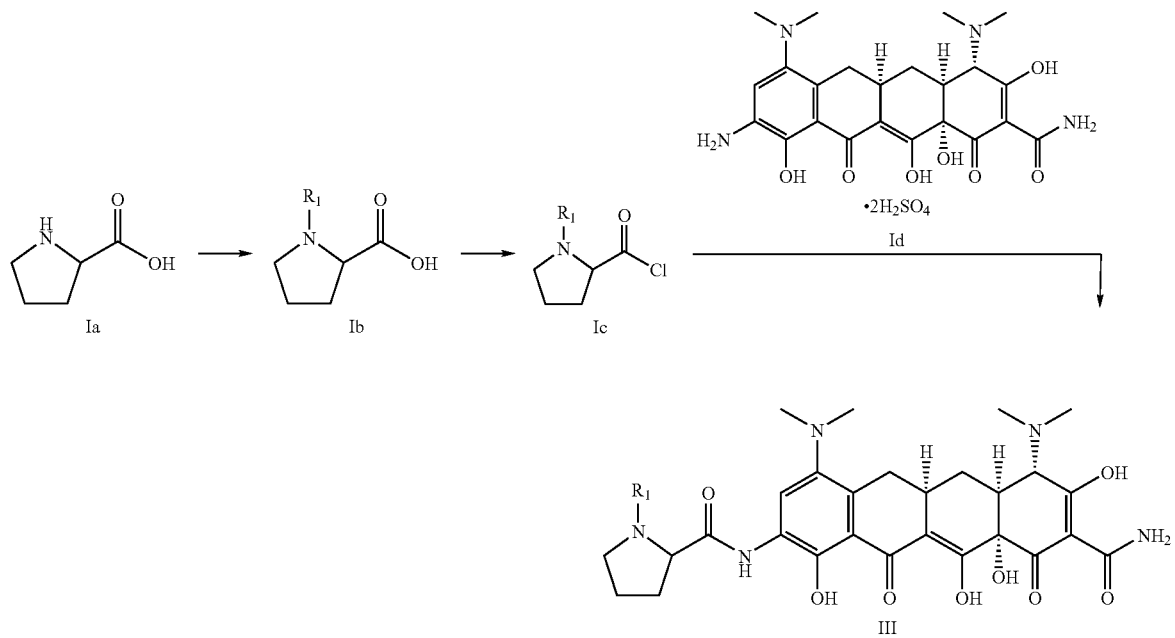

A compound of formula (Ib) may be prepared by reductive amination of corresponding carbonyl compound with compound of formula (Ia) in presence of at least one reducing agent, such as $NaCNBH_3$, $Na(OAc)_3BH_3$, $NaBH_4$, Pd/C, $Pd(OH)_2$, under hydrogen atmosphere in a solvent, such as methanol, ethanol, THF and the like; at a temperature in the range of from about $-10°$ C. to about $80°$ C., over a period of from about 5 min to about 12 hours.

Alternatively, a compound of general formula (III) may also be prepared by reacting a compound of formula (Ib) with a compound of formula (Id) in the presence of reagents, such as DCC, HOBT, EDCC and the like in solvents such as DCM, DMF, DMPU, THF, $CH_3CN$ and the like.

The compound of general formula (I) may also be prepared as illustrated in Scheme (II).

Scheme II

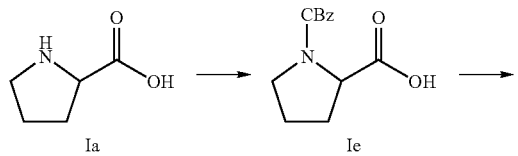

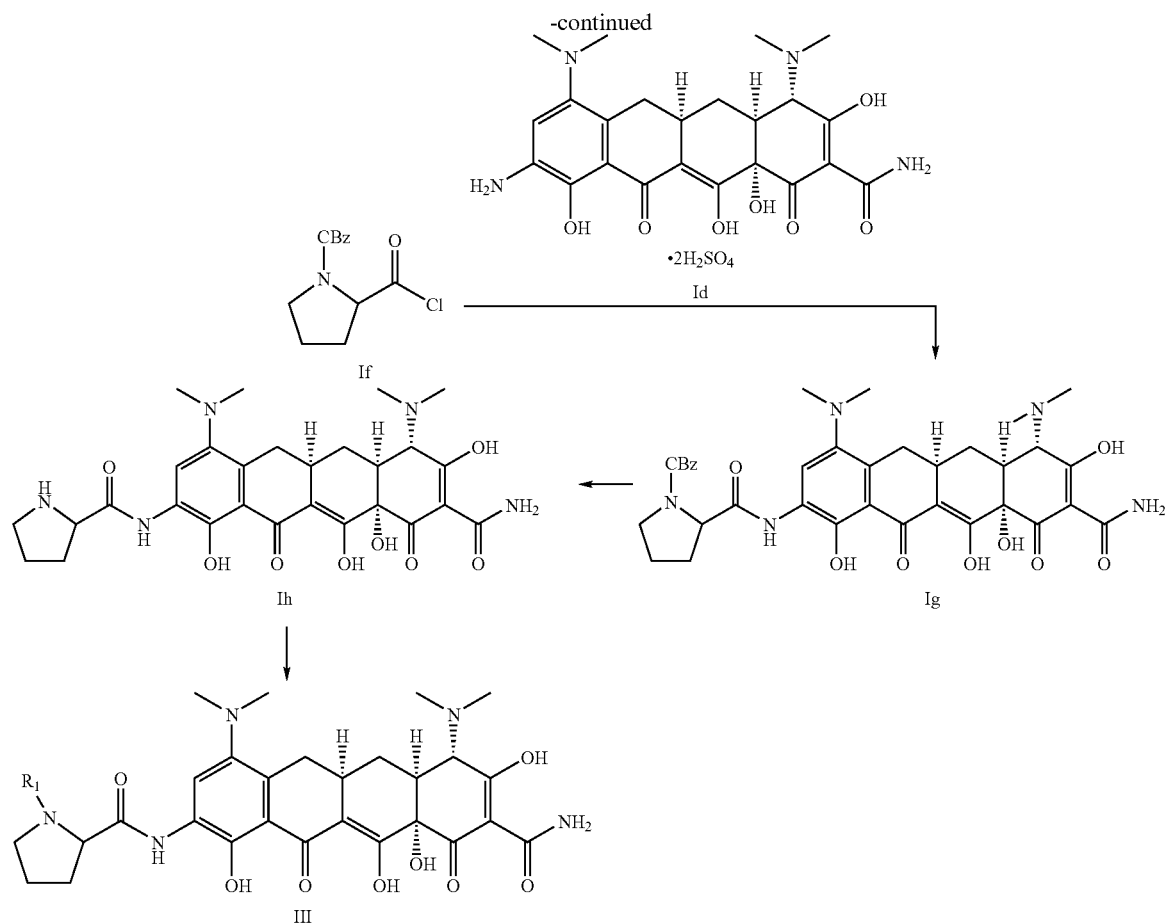

A compound of general formula (Ie) may be prepared by reacting compound of formula (Ia) with benzyl chloroformate (CBz-Cl) in presence of a solvent such as dioxane-water, DCM, THF, CH$_3$CN, DMF, and the like; in a base such as K$_2$CO$_3$, Na$_2$CO$_3$, NaHCO$_3$, Et3N, Hunig's base, and the like; at a temperature in the range of from about 0° C. to about 60° C., over a period of from about 30 min to about 6 hours.

Compounds of general formula (If) and (Ig) may be obtained by following the similar procedure as described in Scheme 1.

Deprotection (of the CBz group) may be conducted by hydrogenating a compound of formula (Ig) with at least one reagent, such as 10% Pd charcoal, Pd(OH)$_2$, (PPh$_3$)$_3$RhCl, in a solvent such as ethylacetate, methanol, THF or dioxane, at a temperature in the range of from about 0° C. to about 60° C., over a period of from about 5 min to about 6 hours to afford a compound of formula (Ih).

The compound of general formula (I) may be obtained by reductive amination of a compound of formula (Ih) in presence of reducing agent, such as cyanoborohydride (NaBH$_3$CN) or sodium triacetoxyborohydride (NaBH(OC-OCH$_3$)$_3$), in solvent such as methanol, ethanol, THF and the like and primary amines such as triethylamine, catalyst such as indium chloride (InCl$_3$), at a temperature in the range of from about −10° C. to about 80° C., over a period of from about 5 min to about 12 hours, and/or as disclosed in scheme 1.

Compounds of the invention were named by Chemdraw ultra version 11.0.1 (developed by ChembridgeSoft corporation) or were given names which appeared to be consistent with Chemdraw nomenclature.

All eluents for column or thin layer chromatography were prepared and reported as volume: volume (v:v) solutions. The quantities of solvents and reagents used for reaction work-up or product isolation are those typically used by one having ordinary skill in the art of organic chemical synthesis, and the quantity of these solvents and reagents used is determined based upon synthetic experience and appropriateness to the specific reaction. For example: 1) crushed ice quantity typically ranged from about 10-1000 grams depending on reaction scale; 2) silica gel quantity used in column chromatography depended on material quantity, complexity of mixture, and size of chromatography column employed and typically ranged from about 5-1000 grams; 3) extraction solvent volume ranged from about 10-500 mL depending on reaction size; 4) washes employed in compound isolation ranged from about 10-100 mL of solvent or aqueous reagent depending on scale of reaction; and 5) drying reagent amounts (potassium carbonate, sodium carbonate, magnesium sulfate, and the like) typically ranged from about 5-100 grams depending on the amount of solvent to be dried and its water content.

The following examples describe further embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLES

The novel compounds of the present invention were prepared according to the procedure of the following schemes and examples, using appropriate materials and are further exemplified by the following specific examples. These compounds are not, however, to be construed as forming the only genus that is considered as the invention, and any combination of the compounds or their moieties may itself form a genus. The following examples further illustrate details for the preparation of the compounds of the present invention. Those having ordinary skill in the art will understand that known variations of the conditions and processes of the following preparative procedures can be used to prepare these compounds. All temperatures are degrees Celsius unless otherwise noted.

Preparation 1

Preparation of (S)-1-isopropylpyrrolidine-2-carboxylic acid

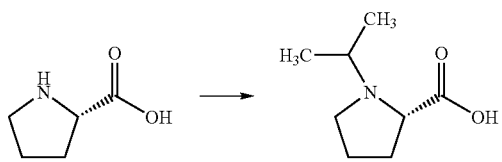

A suspension of (S)-pyrrolidine-2-carboxylic acid (5 g, 50 mmol), acetone (5.52 mL, 50 mmol) and 10% Pd/C (2.5 g) in methanol (100 mL) was stirred under hydrogen atmosphere for 6 to 12 hours. The reaction mixture was filtered on a pad of celite and the filtrate was concentrated. The residue obtained was filtered through a column of silica gel to afford (S)-1-isopropylpyrrolidine-2-carboxylic acid (8.0 g, 94%) as a colorless solid.

$^1$H NMR (D2O, 200 MHz): δ 4.15-4.03 (m, 1H), 3.72-3.57 (m, 2H), 3.26-3.15 (m, 1H), 2.48-2.39 (m, 1H), 2.15-1.97 (m, 3H), 1.35 (t, J=2.9 Hz 6H).

The following intermediates were prepared according to a similar procedure described as above, by utilizing appropriate starting materials:

| No. | Structure | $^1$H NMR |
|---|---|---|
| 2. | ![CH3 on N-pyrrolidine-COOH] | (D$_2$O, 400 MHz): δ 3.98-3.94 (m, 1H), 3.84-3.78 (m, 1H), 3.26-3.19 (m, 1H), 3.00 (s, 3H), 2.60-2.53 (m, 1H), 2.30-2.03 (m, 3H). |
| 3. | ![(CH3)2CHCH2-N-pyrrolidine-COOH] | (CD$_3$OD, 200 MHZ); 3.86-3.77 (m, 2H); 3.12-3.06 (m, 2H); 3.00-2.96 (m, 1H); 2.45-2.36 (m, 1H); 2.18-1.92 (m, 4H); 1.06 (t, J = 6.3 Hz, 6H) |
| 4. | ![(CH3)3C-CH2-N-pyrrolidine-COOH] | (CD$_3$OD, 200 MHZ); 3.95-3.88 (m, 2H); 3.31-3.03 (m, 3H); 2.42-2.33 (m, 1H); 2.16-2.05 (m, 2H); 2.02-1.90 (m, 1H); 1.11 (S. 9H). |
| 5. | ![CH3-N-pyrrolidine-COOH] | (CD$_3$OD, 400 MHz): δ 3.79-3.76 (m, 1H), 3.76-3.65 (m, 1H), 3.13-3.06 (m, 1H), 2.91 (s, 3H), 2.51-2.41 (m, 1H), 2.16-2.06 (m, 2H), 2.02-1.90 (m, 1H) |

Preparation 6

Preparation of (S)-1-ethylpyrrolidine-2-carboxylic acid

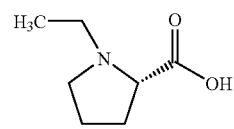

Step: 1

To a solution of L-proline benzyl ester .TFA salt (6 g, 18.81 mmol) in dry DMF (15 mL) was added successively acetaldehyde (1.655 g, 37.61 mmol), triethylamine (10.5 mL, 75.24 mmol), sodium cyanoborohydride (2.57, 37.61 mmol) and InCl$_3$ (416 mg, 1.881 mmol) at ice bath temperature (0-10° C.) under argon atmosphere. The reaction mixture was stirred at room temperature (20-35° C.) over 12 h and then quenched with methanol (5 ml). The reaction mixture was dissolved in water and extracted with ethyl acetate. The organic layer was washed several times with water and collected over anhydrous Na$_2$SO$_4$. The solvent was removed under reduced pressure and the residue was purified by column chromatography.

Step: 2

A suspension of 1-ethyl pyrrolidine-2-carboxylic acid benzyl ester (1.5 g, 6.43 mmol) and 10% Pd on charcoal in methanol (30 mL) was hydrogenated over 12 h. The reaction mixture was filtered through a pad of celite and the filtrate was concentrated to get title product (700 mg, 76%).

¹H NMR (CD₃OD, 400 MHZ): δ 3.84-3.80 (m, 1H), 3.74-3.69 (m, 1H), 3.21-3.04 (m, 2H), 2.95-2.90 (m, 1H), 2.54-2.36 (m, 1H), 2.16-2.03 (m, 2H), 1.99-1.87 (m, 1H), 1.21 (t, J=7.3 Hz, 3H).

Preparation 7

Preparation of (S)-1-propylpyrrolidine-2-carboxylic acid

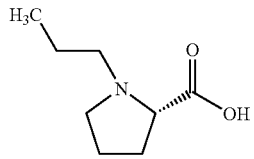

Step: 1

To a solution of L-proline benzyl ester .TFA salt (6 g, 18.81 mmol) in dry DMF (15 mL) was added successively propionaldehyde (2.2 g, 37.61 mmol), triethylamine (10.5 mL, 75.24 mmol), sodium cyanoborohydride (2.57, 37.61 mmol) and InCl₃ (416 mg, 1.881 mmol) at ice bath temperature (0-10° C.) under argon atmosphere. The reaction mixture was stirred at a temperature in the range of 20° C. to 35° C. over 12 h and then quenched with methanol (5 mL). The reaction mixture was dissolved in water and extracted with ethyl acetate. The organic layer was washed several times with water and collected over anhydrous Na₂SO₄. The solvent was removed under reduced pressure and the residue was purified by column chromatography.

Step: 2

A suspension of 1-n-propyl pyrrolidine-2-carboxylic acid benzyl ester (2.0 g, 8.09 mmol) and 10% Pd on charcoal in methanol (30 mL) was hydrogenated over 12 h. The reaction mixture was filtered through a pad of celite and the filtrate was concentrated (1 g, 77%).

¹H NMR (CD₃OD, 400 MHZ): δ 3.85-3.81 (m, 1H), 3.76-3.71 (m, 1H), 3.22-3.15 (m, 1H), 3.11-3.03 (m, 2H), 2.46-2.36 (m, 1H), 2.16-1.99 (m, 2H), 1.98-1.89 (m, 1H), 1.79-1.68 (m, 2H), 1.00 (t, J=7.3 Hz, 3H).

Preparation 8

Preparation of (S)-1-(benzyloxycarbonyl)pyrrolidine-2-carboxylic Acid

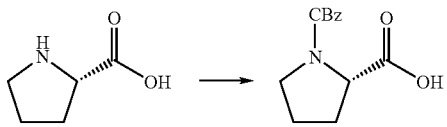

To an ice cold solution of (S)-pyrrolidine-2-carboxylic acid (2 g, 19.8 mmol) in 5:1 dioxane-water (15 mL) was added successively K₂CO₃ (4 g, 29.7 mmol) and CBz-Cl (4 g, 23.7 mmol). The reaction mixture was treated at a temperature in the range of 20° C. to 35° C. over a period of 12 h. The volatiles were evaporated under reduced pressure and the residue was worked up with chloroform. The crude product obtained was further purified by column chromatography to afford (S)-1-(benzyloxycarbonyl)pyrrolidine-2-carboxylic acid (2.2 g, 47.8%).

¹H NMR (DMSO-d⁶ 200 MHz): δ 12.56 (s, 1H), 7.38-7.09 (m, 5H), 5.11-5.03 (m, 2H), 4.27-4.14 (m, 1H), 3.46-3.36 (m, 2H), 2.290-2.12 (m, 2H), 1.91-1.82 (m, 2H).

Example 1

Synthesis of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-isopropylpyrrolidine-2-carboxamide Step 1: Synthesis of (S)-1-isopropylpyrrolidine-2-carbonyl Chloride

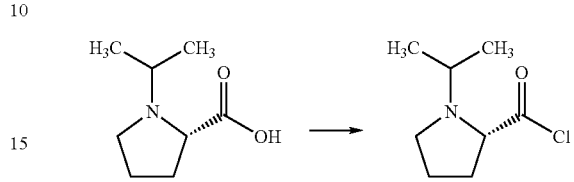

To a solution of (S)-1-isopropylpyrrolidine-2-carboxylic acid (4 g, 23.4 mmol) in dry dichloromethane (40 mL) was added oxalyl chloride (4.4 mL, 46.8 mmol) drop wise under nitrogen at ice bath temperature (0-10° C.). After stirring for 5 min, a drop of dry DMF was added to the reaction mixture and was allowed to stir for 2 h at the same temperature. The volatiles were removed on a rotavapor at reduced pressure and the residue was allowed to stay at high vacuum pump for 1 h to afford (S)-1-isopropylpyrrolidine-2-carbonyl chloride.

Step 2: Synthesis of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-isopropylpyrrolidine-2-carboxamide

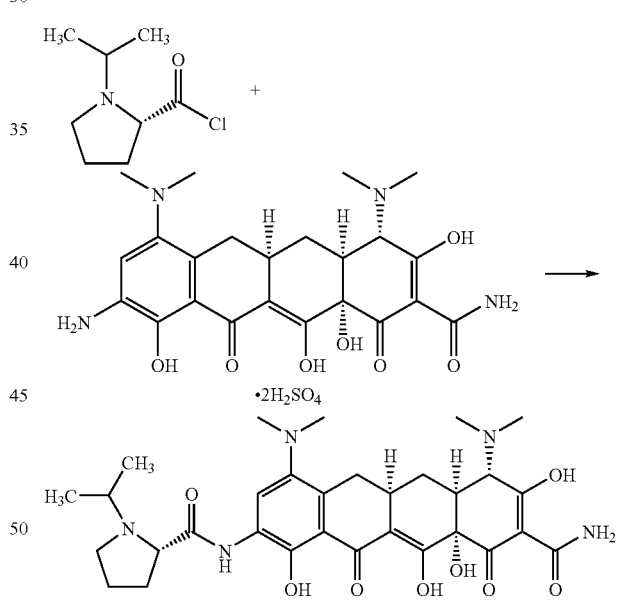

(S)-1-isopropylpyrrolidine-2-carbonyl chloride obtained above was slowly added in portions to a stirred suspension of 9-aminominocycline disulfate (6-g, 9 mmol) and anhydrous Na₂CO₃ (3.8 g, 35.9 mmol) in 1:4 acetonitrile-DMPU (125 mL) at a temperature in the range of 20° C. to 35° C. under nitrogen. After stirring for 10 min, methanol (~10 mL) was added to the reaction mixture and was filtered. The filtrate was poured into ether to obtain a yellow colored solid. The ether was decanted and then the sticky residue was dissolved in water and extracted with chloroform by slowly basifying with aq. NH₃. The organic layer was washed several times with water and collected over anhydrous Na₂SO₄. The solvent was removed under reduced pressure and the residue was dried under high vacuum. The product was triturated with petroleum ether to obtain amorphous brown solid. The resultant solid was dried in a vacuum pump to afford (S)—N-((5aR, 6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-isopropylpyrrolidine-2-carboxamide (2.5 g, 31%).

¹H NMR (CD₃OD, 400 MHz): δ 8.38 (s, 1H), 3.40-3.37 (m, 1H), 3.25-3.22 (m, 2H). 3.00-2.81 (m, 4H), 2.64-2.40 (m, 14H), 2.17-1.96 (m, 3H), 1.80-1.61 (m, 3H), 1.37-1.26 (m, 6H).

Example 2

Preparation of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-methylpyrrolidine-2-carboxamide

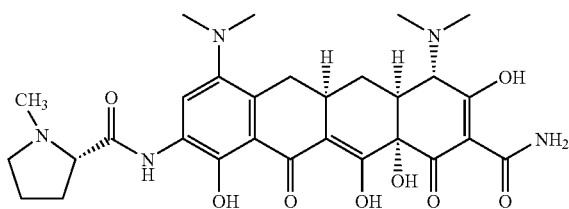

To a solution of the 9-amino minocycline (5.5 g, 8.2 mmol) in a 1:4 mixture of acetonitrile (5 mL) and DMPU (20 mL), was added anhydrous Na₂CO₃. The reaction mixture was stirred at ice temp for 5 min and the solid acid chloride (27.8 mmol), obtained using the procedure described in example 1, was added at the same temp under inert atmosphere. Stirring was continued for an additional 30 min. The reaction mixture was quenched with methanol (5 mL) and was decanted slowly into diethyl ether (1 L). The ether was decanted and then the sticky residue was dissolved in water and extracted with chloroform by slowly basifying with aq. NH₃. The organic layer was washed several times with water and collected over anhydrous Na₂SO₄. The solvent was removed under reduced pressure and the residue was dried under high vacuum. The product was triturated with petroleum ether to obtain amorphous brown solid. This material was re-crystallized from 30 mL of hot ethanol (50-55° C.) to furnish title compound as bright yellow solid (1.6 g, 34%).

¹H NMR (DMSO, 400 MHz): δ 11.95 (brs, 1H), 9.71 (s, 1H), 9.12 (brs 1H), 8.41 (S, 1H), 3.52-3.10 (m, 3H), 3.00-2.92 (m, 1H), 2.92-2.80 (m, 1H), 2.61-2.05 (m, 24H), 1.89-1.65 (m, 3H), 1.65-1.54 (m, 1H).

Example 3

Preparation of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-ethylpyrrolidine-2-carboxamide

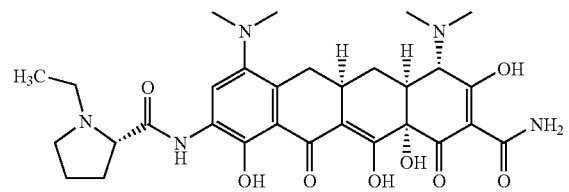

To a solution of the 9-amino minocycline (160 mg, 0.24 mmol) in a 1:4 mixture of acetonitrile (1 mL) and DMPU (4 mL), was added anhydrous Na₂CO₃. The reaction mixture was stirred at ice temp for 5 min and the solid acid chloride (0.46 mmol) obtained using the procedure described in example 1 was added at the same temp under inert atmosphere. Stirring was continued for an additional 30 min. The reaction mixture was quenched with methanol (2 mL) and was decanted slowly into diethyl ether (150 ml). The ether was decanted and then the sticky residue was dissolved in water and extracted with chloroform by slowly basifying with aq. NH₃. The organic layer was washed several times with water and collected over anhydrous Na₂SO₄. The solvent was removed under reduced pressure and the residue was dried under high vacuum. The product was triturated with petroleum ether to obtain title compound as amorphous yellow solid. (0.020 g, 14%).

¹H NMR (CD₃OD, 400 MHz): δ 8.42 (s, 1H), 3.42-3.35 (m, 2H), 3.20-3.15 (m, 2H), 2.80-2.75 (m, 1H), 2.60 (s, 12H), 2.50-1.62 (m, 11H), 0.98 (t, J=7.3 Hz, 3H)

Example 4

Preparation of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-propylpyrrolidine-2-carboxamide

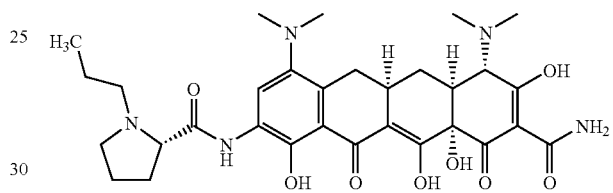

To a solution of the 9-amino minocycline (500 mg, 0.75 mmol) in a 1:4 mixture of acetonitrile (2 mL) and DMPU (8 mL), was added anhydrous Na₂CO₃. The reaction mixture was stirred at ice temp for 5 min and the solid acid chloride (1.48 mmol) obtained using the procedure described in example 1, was added at the same temp under inert atmosphere. Stirring was continued for an additional 30 min. The reaction mixture was quenched with methanol (3 mL) and was decanted slowly into diethyl ether (250 ml). The ether was decanted and then the sticky residue was dissolved in water and extracted with chloroform by slowly basifying with aq. NH₃. The organic layer was washed several times with water and collected over anhydrous Na₂SO₄. The solvent was removed under reduced pressure and the residue was dried under high vacuum. The product was triturated with petroleum ether to obtain amorphous yellow solid. (0.150 g, 33%).

¹H NMR (CD₃OD, 400 MHz): δ 8.42 (s, 1H), 3.42-3.35 (m, 1H), 3.20-3.15 (m, 4H), 2.64-2.35 (m, 15H), 2.30-1.54 (m, 10H), 0.97-0.80 (m, 3H).

Example 5

Preparation of (R)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-methylpyrrolidine-2-carboxamide

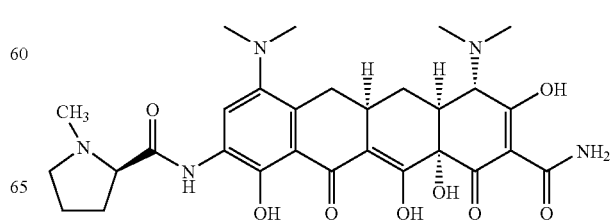

To a solution of the 9-amino minocycline (2.0 g, 2.99 mmol) in a 1:4 mixture of acetonitrile (3 mL) and DMPU (12 mL), was added anhydrous Na$_2$CO$_3$. The reaction mixture was stirred at ice temp for 5 min and the solid acid chloride (7.75 mmol) obtained using the procedure described in example 1 was added at the same temp under inert atmosphere. Stirring was continued for an additional 30 min. The reaction mixture was quenched with methanol (5 mL) and was decanted slowly into diethyl ether (500 ml). The ether was decanted and then the sticky residue was dissolved in water and extracted with chloroform by slowly basifying with aq. NH$_3$. The organic layer was washed several times with water and collected over anhydrous Na$_2$SO$_4$. The solvent was removed under reduced pressure and the residue was dried under high vacuum. The product was triturated with petroleum ether to obtain amorphous brown solid. This material was re-crystallized from 30 mL of hot ethanol (50-55° C.) to furnish title compound as bright yellow solid (0.1 g, 6%). The yield of the product is dependent on purity and amount of crude product before recrystallization.

$^1$H NMR (CD3OD, 400 MHz): δ 8.38 (s, 1H), 4.52 (brs 1H), 3.26-3.20 (m, 2H), 3.13-3.03 (m, 2H), 2.92-2.85 (m, 1H), 2.76-2.46 (m, 16H), 2.42-2.10 (m, 3H), 1.96-1.85 (m, 3H), 1.69-1.63 (m, 1H)

Example 6

Synthesis of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-neopentylpyrrolidine-2-carboxamide dihydrochloride Step 1: Synthesis of (S)-benzyl 2-(chlorocarbonyl)pyrrolidine-1-carboxylate

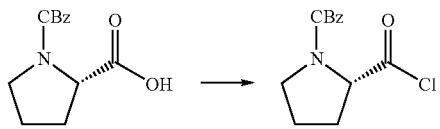

Step 1 was prepared according to a similar procedure described in Example 1 by taking (S)-1-(benzyloxycarbonyl)pyrrolidine-2-carboxylic acid as the starting material.

Step 2: Synthesis of (S)-benzyl 2-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-ylcarbamoyl)pyrrolidine-1-carboxylate

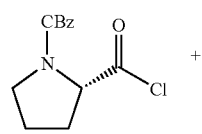

+

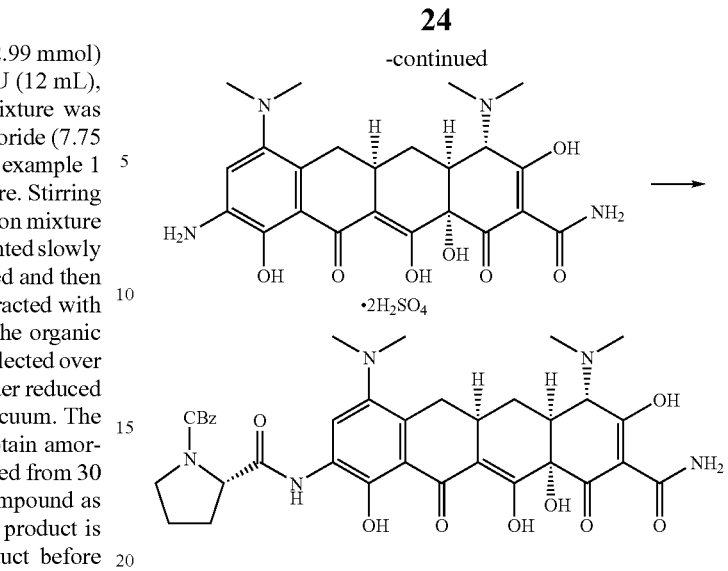

Step 2 was prepared according to a similar procedure described in Example 1 by taking (S)-benzyl 2-(chlorocarbonyl)pyrrolidine-1-carboxylate as the starting material.

Step 3: Synthesis of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)pyrrolidine-2-carboxamide

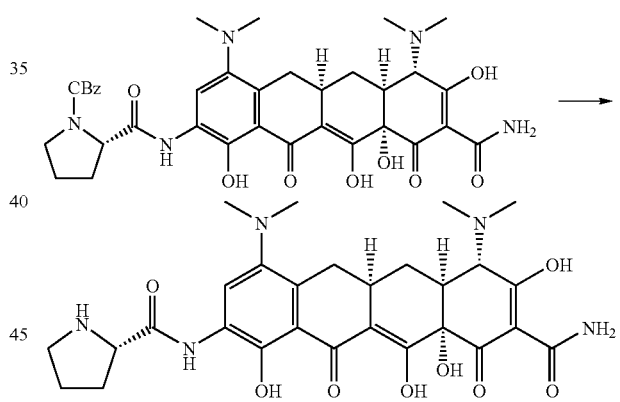

A suspension of (S)-benzyl 2-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-ylcarbamoyl)pyrrolidine-1-carboxylate (200 mg, 0.29 mmol) and 10% Pd on charcoal in methanol (10 mL) was hydrogenated over 1 h. The reaction mixture was filtered through a pad of celite and the filtrate was poured into ether containing HCl to get (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)pyrrolidine-2-carboxamide (120 mg, 72%).

(DMSO, 400 MHz): δ 10.19 (brs, 1H), 9.12 (brs, 1H), 8.35 (s, 2H), 3.93-3.90 (m, 1H), 3.43-3.28 (m, 3H), 3.18-3.13. (m, 1H), 3.07-3.01 (m, 1H), 2.92-2.82 (m, 2H), 2.53-2.50 (m, 7H), 2.45 (s, 6H), 2.30-2.23 (m, 2H), 2.15-2.07 (m, 2H), 1.90-1.82 (m, 1H), 1.74-1.67 (m, 2H), 1.63-1.54 (m, 2H), 1.40-1.23 (m, 1H).

Step 4: Synthesis of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-neopentylpyrrolidine-2-carboxamide dihydrochloride

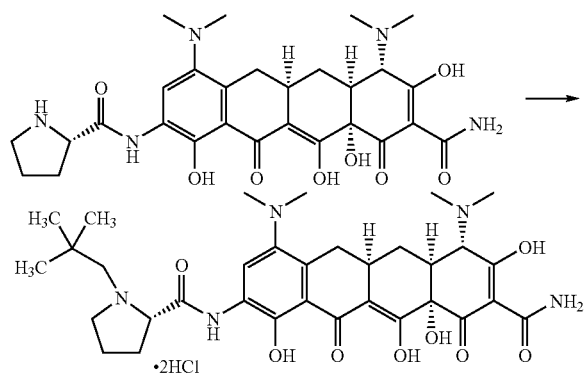

To a solution of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)pyrrolidine-2-carboxamide (500 mg, 0.65 mmol) in dry DMF (3 mL) was added successively pivalaldehyde (67 mg, 0.78 mmol), triethylamine (0.36 mL, 2.6 mmol), sodium cyanoborohydride (49 mg, 0.78 mmol) and InCl$_3$ (17 mg, 0.08 mmol) at ice bath temperature (0-10° C.) under argon atmosphere. The reaction mixture was stirred at a temperature in the range of 20° C. to 35° C. over 2 h, quenched with methanol (1 mL) and decanted slowly into diethyl ether (0.5 L). The ether was decanted and then the sticky residue was dissolved in water and extracted with chloroform by slowly basifying with aq. NH$_3$. The organic layer was washed several times with water and collected over anhydrous Na$_2$SO$_4$. The solvent was removed under reduced pressure and the residue was dried under high vacuum to get (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-neopentylpyrrolidine-2-carboxamide dihydrochloride (30 mg, 7%).

$^1$H NMR: (CD$_3$OD, 400 MHz): δ 8.57 (s, 1H), 4.75-4.52 (m, 2H), 4.16 (s, 1H), 4.06-4.02 (m, 1H), 3.43-2.16 (m, 23H), 1.74-1.64 (m, 1H), 1.15 (s, 9H).

Example 7

Process for Preparation of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)-1-isobutylpyrrolidine-2-carboxamide dihydrochloride

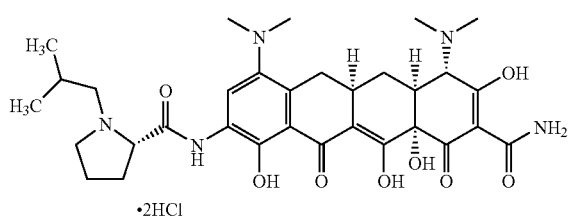

To a solution of (S)—N-((5aR,6aS,7S,10aS)-9-carbamoyl-4,7-bis(dimethylamino)-1,8,10a,11-tetrahydroxy-10,12-dioxo-5,5a,6,6a,7,10,10a,12-octahydrotetracen-2-yl)pyrrolidine-2-carboxamide (500 mg, 0.75 mmol), obtained in example 6, in dry DMF (3 mL) was added successively isobutyraldehyde (67 mg, 0.78 mmol), triethylamine (0.36 mL, 2.6 mmol), sodium cyanoborohydride (49 mg, 0.78 mmol) and InCl$_3$ (17 mg, 0.08 mmol) at ice bath temperature (0-10° C.) under argon atmosphere. The reaction mixture was stirred at a temperature in the range of 20° C. to 35° C. over 2 h and then quenched with methanol (1 mL). was decanted slowly into diethyl ether (0.5 L). The ether was decanted and then the sticky residue was dissolved in water and extracted with chloroform by slowly basifying with aq. NH$_3$. The organic layer was washed several times with water and collected over anhydrous Na$_2$SO$_4$. The solvent was removed under reduced pressure and the residue was dried under high vacuum. The resultant mixture was poured into ether containing HCl to get title compound (80 mg, 17%).

$^1$H NMR: (CD$_3$OD, 400 MHz): δ 8.58 (s, 1H), 4.50 (t, J=8.1 Hz, 1H), 4.16 (s, 1H), 3.94-3.88 (m, 1H), 3.43-2.04 (m, 25H), 1.73-1.64 (m, 1H), 1.13-1.06 (m, 6H).

Example 8

In Vitro Determination of Minimum Inhibition Concentrations (MICs)

Minimum Inhibition Concentrations (MICs) were determined by broth microdilution technique as per the guidelines prescribed in the fifth edition of Approved Standards NCCLS document M7-A5 Vol 20-No 2, 2000 Villinova, Pa. (Currently *Clinical and Laboratory Standards Institute (CLSI)*). Initial stock solution of the compound of formula (I) was prepared in DMSO. Subsequent two fold dilutions were carried out in sterile Cation adjusted Muller Hinton Broth (Difco) (MHB). Frozen cultures stocks were inoculated in 25 ml sterile MHB in 50 ml Erlyn Meyer flasks.
Composition of MHB is as follows: Beef Extract Powder—2.0 grams/litre, Acid Digest of Casein—17.5 grams/litre, Soluble Starch—1.5 grams/litre, Final pH 7.3±0.1

Flasks were incubated for 4 to 5 hours at 36±1° C. on a rotary shaker at 110 rpm. Inoculum was prepared by diluting the culture in sterile MHB to obtain a turbidity of 0.5 McFarland standard. This corresponds to 1–2×10$^8$ CFU/mL. The stock was further diluted to achieve a final inoculum density of 5×10$^4$ to 1×10$^5$ CFU/well. The plates were incubated 18 to 20 hours at 37° C.

MIC is read as the lowest concentration of the compound that completely inhibits growth of the organism in the microdilution wells as detected by the unaided eye.

| Organism | Culture No. |
|---|---|
| Article I. *Staphylococcus aureus* | ATCC 33591 |
| *Staphylococcus aureus* | ATCC 49951 |
| *Staphylococcus aureus* | ATCC 29213 |
| Article II. *Enterococcus faecalis* | ATCC 29212 |
| *Enterococcus faecalis* | NCTC 12201 |
| *Enterococcus faecium* | NCTC 12202 |
| *Escherichia coli* | ATCC 25922 |
| *Haemophilus influenzae* | ATCC 49247 |
| *Klebsiella pneumoniae* | ATCC 700603 |
| *Pseudomonas aeruginosa* | ATCC 27853 |
| *Haemophilus influenzae* | ATCC 49766 |
| *Haemophilus influenzae* | ATCC 9006 |
| *Moraxella catarrhalis* | ATCC 25238 |
| *Streptococcus pneumoniae* | ATCC 6303 |

-continued

| Organism | Culture No. |
|---|---|
| Streptococcus pneumoniae | ATCC 49619 |
| Streptococcus pneumoniae | ATCC 700673 |
| Streptococcus mutans | |
| S. aureus - MRSA | DRCC 446 |
| Viridans Streptococci & Streptococcus Spp | |

ATCC: American Type Culture Collection, USA
NCTC: National Collections of Type Cultures, Colindale, UK
DRCC: Dr. Reddy's Culture Collection, Hyderabad, India.
MSSA: Methicillin sensitive *staphylococcus aureus*
MRSA: Methicillin resistant *staphylococcus aureus*
VSE: Vancomycin sensitive *Enterococcus*
VRE: Vancomycin resistant *Enterococcus*
K. pn: K pneumoniae
P. aeru: P. aeruginosa The in vitro antibacterial activity data is shown in TABLE 1:

TABLE 1

| | MIC (µg/ml) | | | | | | | |
|---|---|---|---|---|---|---|---|---|
| | S. aureus | | E. faecalis | | E. faecium | E. coli | K. pn | P. aeru |
| Example No. | DRCC 035 MSSA ATCC 29213 | DRCC 019 MRSA ATCC 33591 | DRCC 034 VSE ATCC 29212 | DRCC 153 VRE NCTC 12201 | DRCC 154 VRE NCTC 12202 | DRCC 018 ATCC 25922 | DRCC 575 ATCC 700603 | DRCC 024 ATCC 27853 |
| 2 | 0.12 | 0.25 | 0.03 | 0.03 | 0.01 | 0.12 | 8 | 16 |
| 3 | 0.5 | 0.5 | 0.12 | 0.12 | 0.06 | 0.5 | 16 | >32 |
| 4 | 1 | 1 | 0.25 | 0.5 | 0.12 | 2 | >32 | >32 |
| 7 | 2 | 2 | 0.5 | 1 | 0.5 | 4 | 128 | 64 |

Example 9

Determination of Effective Dose 50 ($ED_{50}$) in Murine Systemic Infection Model Animals: Specific pathogen free outbred, female and male Swiss Albino Mice, 4-6 weeks old, weighing 25±2 grams.
Procedure
Inoculum Preparation:
Systemic infection model is performed based on $LD_{50}$ of an organism. 10-1000×$LD_{50}$ or 1-5 MLD (minimum lethal dose) is used as an infecting inoculum.
Organisms are sub-cultured on blood agar plates and incubated at 35-37° C. for 18-24 hours. Inoculum is prepared in 0.9% normal saline and optical density adjusted at 560 nm to yield an inoculum density of $10^5$ to $10^9$ CFU/mL based on the test organism.
Adjusted inoculum is further diluted 1:1 in mucin solution to achieve a final mucin concentration of 5-7.5% (wt/vol).
Log CFUs of inoculum is determined by serially diluting the inoculum in normal saline and plating on suitable agar plates. Plates are incubated at 35-37° C. for 18-24 hours and counts determined.
Infection:
Animals are infected with 0.5 ml of inoculum by intraperitoneal route.
Two groups of mice left untreated, serve as untreated control.
Treatment:
For single dose, compound of formula (I) is administered at 0 to 3 hour post-infection by p.o./s.c./i.v. route.
For b.i.d., compound of formula (I) administered at 0 to 3 hour post-infection for first dose and at 4 to 6 hours post-infection for second dose by p.o./s.c./i.v. route.
End point: Survival/death in each treated and untreated groups are monitored for 5 days (7 days for *S. pneumoniae*). The $ED_{50}$ values are determined by probit analysis.

REFERENCES (i) Jan G. Den Hollander, Jenny D. Knudsen, Johan W. Mouton, Kurt Fuursted, Niels Frimodt-Moller, Henri A. Verbrugh and Frank Espersen. Comparison of Pharmacodynamics of Azithromycin and Erythromycin In Vitro and In Vivo. Antibacterial agents and chemotherapy. February 1998, p. 377-382 Vol. 42, No. 2 & (ii) Hiroki Okamoto, Shuichi Miyazaki, Kazuhiro Tateda, Yoshikazu Ishii and Keizo Yamaguchi. In Vivo Efficacy of Telithromycin (HMR3647) against *Streptococcus pneumoniae* and *Haemophilus influenzae*. Antibacterial agents and chemotherapy November 2001, p. 3250-3252 Vol. 45, No. 11 The in vivo antibacterial activity data of Example-2 is shown in TABLE 2.

TABLE 2

| | ED50 Values (mg/kg) | |
|---|---|---|
| Organism | p.o.-b.i.d. | i.v.-q.d. |
| MRSA DRCC 446 | 7.3 | 0.77 |
| E faecalis DRCC 543 | 2.53 | 0.28 |
| S. pneumoniae ATCC 49619 | 6.2 | 0.16 |
| E. Coli ATCC 25992 | 12.6 | 0.50 |
| S. aureus DRCC 035 (ATCC 29213) | 5.5 | 0.6 | p.o.—per oral
i.v.—intravenous
s.c—subcutaneous
q.d.—quaque die (once a day)
b.i.d.—bis in die (twice a day)
DRCC—Dr. Reddy's Culture Collection
ATCC—American Type Culture Collection.

All references cited in this specification, are hereby incorporated by reference into this specification in their entireties.
The discussion of the references herein is intended merely to summarize the assertions made by their authors and no admission is made that any reference constitutes prior art. Applicants reserve the right to challenge the accuracy and pertinency of the cited references.
Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

We claim:
1. The compound of general formula (I)

(I)

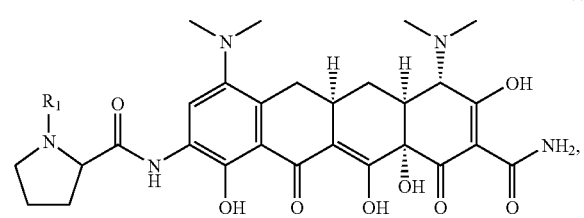

its stereoisomers thereof and/or its pharmaceutical acceptable salts thereof
wherein
$R_1$ is selected from optionally substituted alkyl.
2. The compound as claimed in claim 1, is (II)

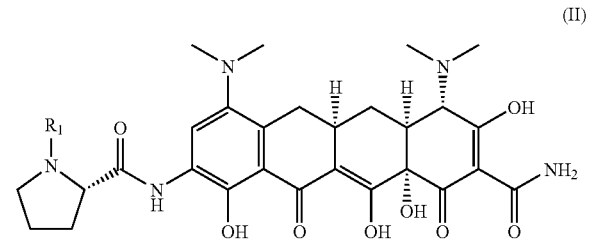

its stereoisomers thereof and/or its pharmaceutical acceptable salts thereof
wherein
$R_1$ is selected from optionally substituted alkyl.
3. The compound as claimed in claim 1, is (III)

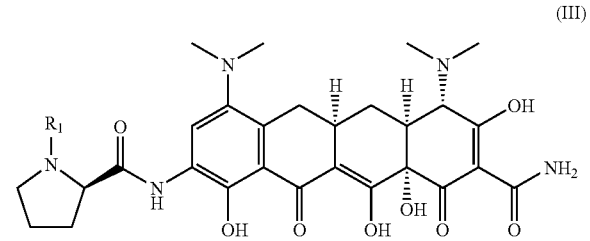

its stereoisomers thereof and/or its pharmaceutical acceptable salts thereof
wherein
$R_1$ is selected from optionally substituted alkyl.
4. The compound as claimed in claim 1, wherein $R_1$ is $(C_1$-$C_5)$ alkyl.
5. The compound as claimed in claim 1, wherein $R_1$ is methyl, ethyl, n-propyl, iso-propyl, n-butyl or iso-butyl.
6. The compound as claimed in claim 1, wherein the compound is one or more of

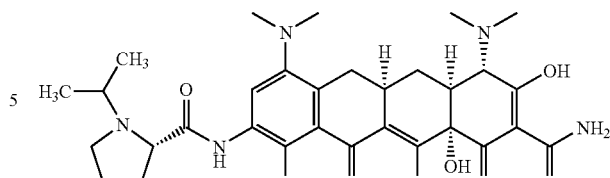

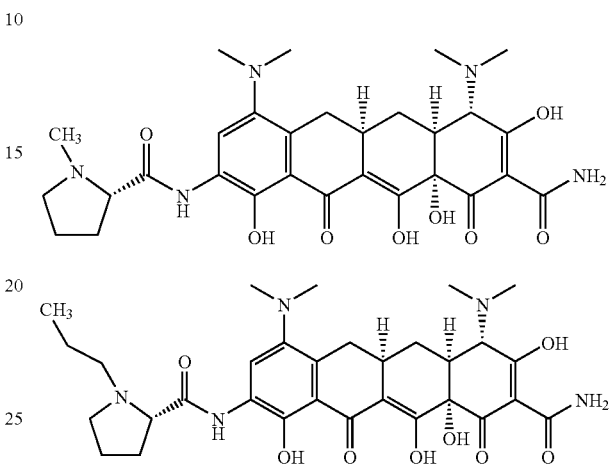

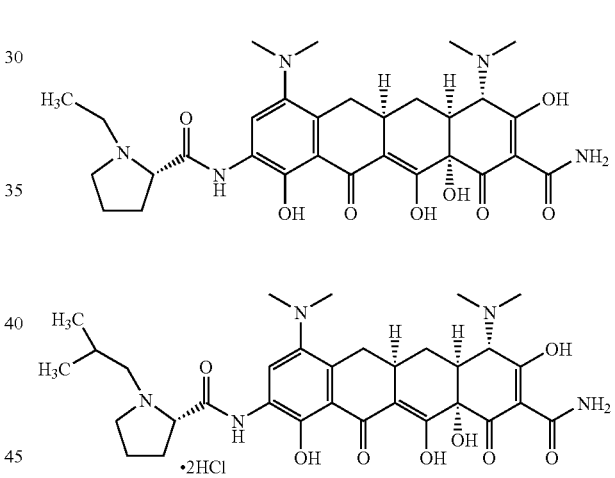

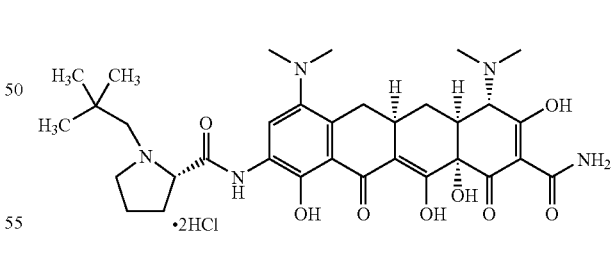

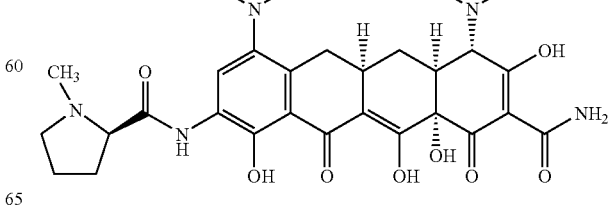

and/or its pharmaceutical acceptable salts thereof.

7. The compound as claimed in claim 1, wherein the compound has the structure:

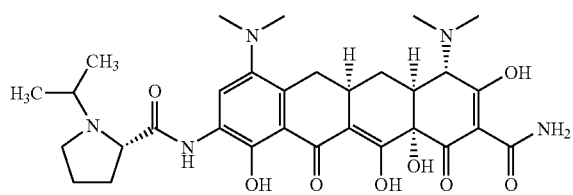

and/or its pharmaceutical acceptable salts thereof.

8. The compound as claimed in claim 1, wherein the compound has the structure:

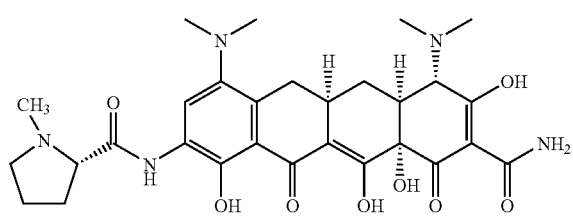

and/or its pharmaceutical acceptable salts thereof.

9. The compound as claimed in claim 1, wherein the compound has the structure:

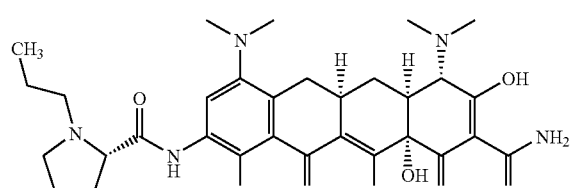

and/or its pharmaceutical acceptable salts thereof.

10. The compound as claimed in claim 1, wherein the compound has the structure:

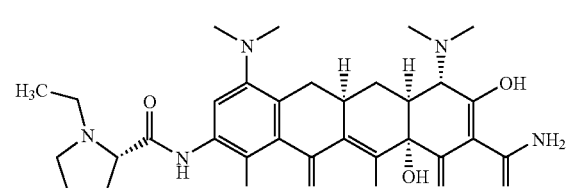

and/or its pharmaceutical acceptable salts thereof.

11. The compound as claimed in claim 1, wherein the compound has the structure:

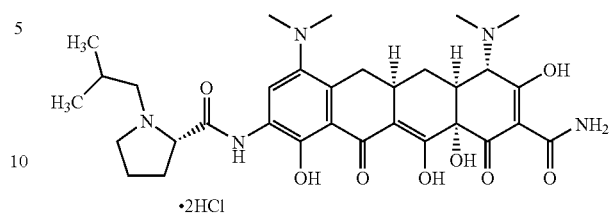

and/or its pharmaceutical acceptable salts thereof.

12. The compound as claimed in claim 1, wherein the compound has the structure:

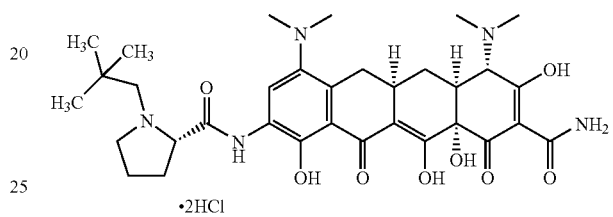

and/or its pharmaceutical acceptable salts thereof.

13. The compound as claimed in claim 1, wherein the compound has the structure:

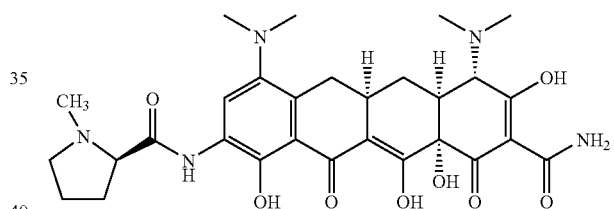

and/or its pharmaceutical acceptable salts thereof.

14. A pharmaceutical composition comprising a pharmaceutically acceptable carrier and at least one compound having the general formula (I), its stereoisomers thereof and/or its pharmaceutically acceptable salts thereof, as claimed in claim 1.

15. A method for the treatment of a bacterial infection in a subject, which comprises administering to the subject a therapeutically effective amount of a compound of formula (I), its stereoisomers thereof, and/or its pharmaceutically acceptable salt thereof.

16. The method of claim 15, wherein said bacterial infection is a Gram-negative or Gram-positive bacterial infection.

* * * * *